United States Patent
Pedragosa-Moreau et al.

(10) Patent No.: US 9,506,095 B2
(45) Date of Patent: Nov. 29, 2016

(54) PROCESS FOR THE ENZYMATIC SYNTHESIS OF (7S)-3,4-DIMETHOXYBICYCLO[4.2.0]OCTA-1,3,5-TRIENE-7-CARBOXYLIC ACID OR ESTERS THEREOF, AND APPLICATION IN THE SYNTHESIS OF IVABRADINE AND SALTS THEREOF

(71) Applicant: LES LABORATOIRES SERVIER, Suresnes (FR)

(72) Inventors: Sandrine Pedragosa-Moreau, Orleans (FR); François Lefoulon, Orleans (FR)

(73) Assignee: LES LABORATORIES SERVIER, Suresnes (FR)

( * ) Notice: Subject to any disclaimer, the term of this patent is extended or adjusted under 35 U.S.C. 154(b) by 431 days.

(21) Appl. No.: 13/759,382

(22) Filed: Feb. 5, 2013

(65) Prior Publication Data
US 2013/0210091 A1 Aug. 15, 2013

(30) Foreign Application Priority Data
Feb. 9, 2012 (FR) ...................... 12 51195

(51) Int. Cl.
| C12P 41/00 | (2006.01) |
| C12P 17/10 | (2006.01) |
| C12P 7/40 | (2006.01) |
| C12P 7/62 | (2006.01) |
| C12P 13/00 | (2006.01) |
| C07C 67/08 | (2006.01) |
| C07C 51/08 | (2006.01) |
| C07C 213/02 | (2006.01) |
| C07C 231/02 | (2006.01) |
| C07D 223/16 | (2006.01) |

(52) U.S. Cl.
CPC .............. C12P 17/10 (2013.01); C07C 51/08 (2013.01); C07C 67/08 (2013.01); C07C 213/02 (2013.01); C07C 231/02 (2013.01); C12P 7/40 (2013.01); C12P 7/62 (2013.01); C12P 13/001 (2013.01); C12P 41/005 (2013.01); C07B 2200/07 (2013.01); C07C 2102/06 (2013.01); C07D 223/16 (2013.01); C12Y 301/01 (2013.01); Y02P 20/52 (2015.11)

(58) Field of Classification Search
CPC ........... C12P 7/40; C12P 7/62; C12P 13/001; C12P 17/10; C12P 41/005; C07C 231/02; C07C 213/02; C07C 67/08; C07C 51/08; C07C 2102/06; C12Y 301/01; C07D 223/16; Y02P 20/52; C07B 2200/07
See application file for complete search history.

(56) References Cited

U.S. PATENT DOCUMENTS

| 5,089,637 | A | * | 2/1992 | Urban | ................. | C07D 311/58 |
| | | | | | | 549/398 |
| 8,288,581 | B2 | | 10/2012 | Peglion et al. | | |
| 2006/0141591 | A1 | * | 6/2006 | Kyuuko et al. | ............... | 435/125 |
| 2011/0251407 | A1 | * | 10/2011 | Kyuuko | ........................ | 549/405 |

FOREIGN PATENT DOCUMENTS

| EP | 2145871 | 1/2010 |
| WO | WO 2011/138625 | 11/2011 |

OTHER PUBLICATIONS

French Preliminary Search Report for FR1251195 of Oct. 19, 2012.
H. Fazzlena, et al., Bioprocess and Biosystems Engineering, vol. 28, No. 4, pp. 227-233, Mar. 1, 2006.
Han-Yuan Lin, et al, Journal of Molecular Catalysis B:: Enzymatic, vol. 24-25. p. 111-120, Oct. 1, 2003.
Jorg Pietruszka, et al., European Journal of Organic Chemistry, vol. 2009. No. 35, p. 6217-6224, Dec. 1, 2009.
M. Paravidino, et al., "Chapter 8.2.2.1 Resolution of carboxylates with a non-functionalized stereogenic center at the alpha-position" In: Drauz, et al, "Enzyme Catalysis in Organic Synthesis". vol. 1, pp. 266-270, Feb. 1, 2012.
Manual of Clinical Enzyme Measurements, Worthington Biochemical Corporation, Freehold, NJ (1972), available at http://www.worthington-biochem.com/introBiochem/Enzymes.pdf.

* cited by examiner

Primary Examiner — Renee Claytor
Assistant Examiner — Susan E Fernandez
(74) Attorney, Agent, or Firm — Hueschen and Sage

(57) ABSTRACT

Process for the enzymatic synthesis of the compound of formula (I):

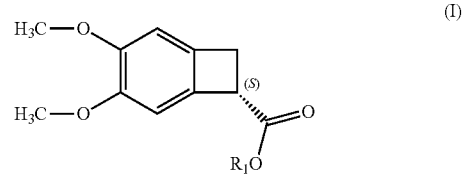

wherein $R_1$ represents a hydrogen atom or an alkyl group. Application in the synthesis of ivabradine and addition salts thereof with a pharmaceutically acceptable acid.

13 Claims, 2 Drawing Sheets

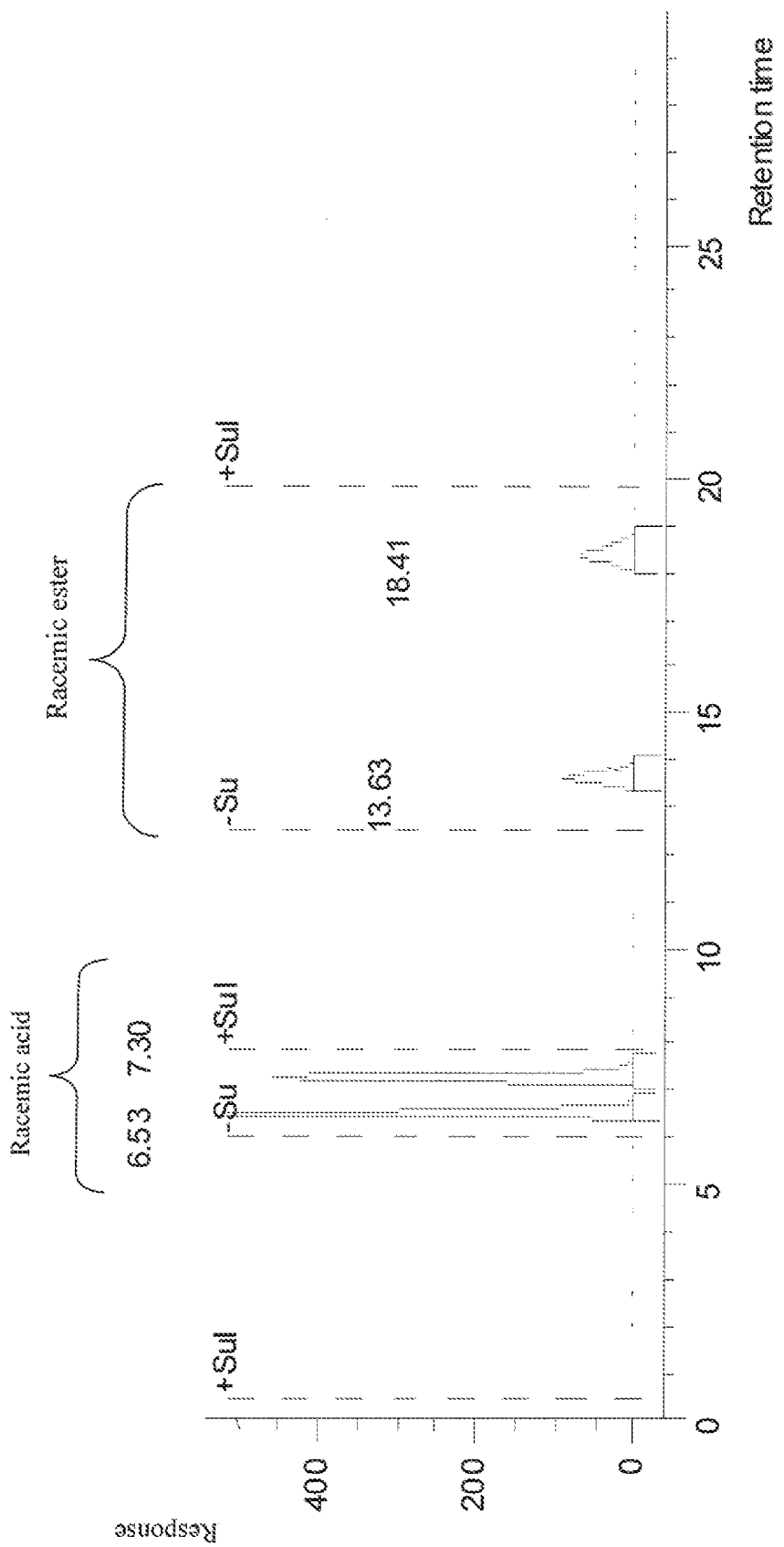
Figure 1 – racemic mixture

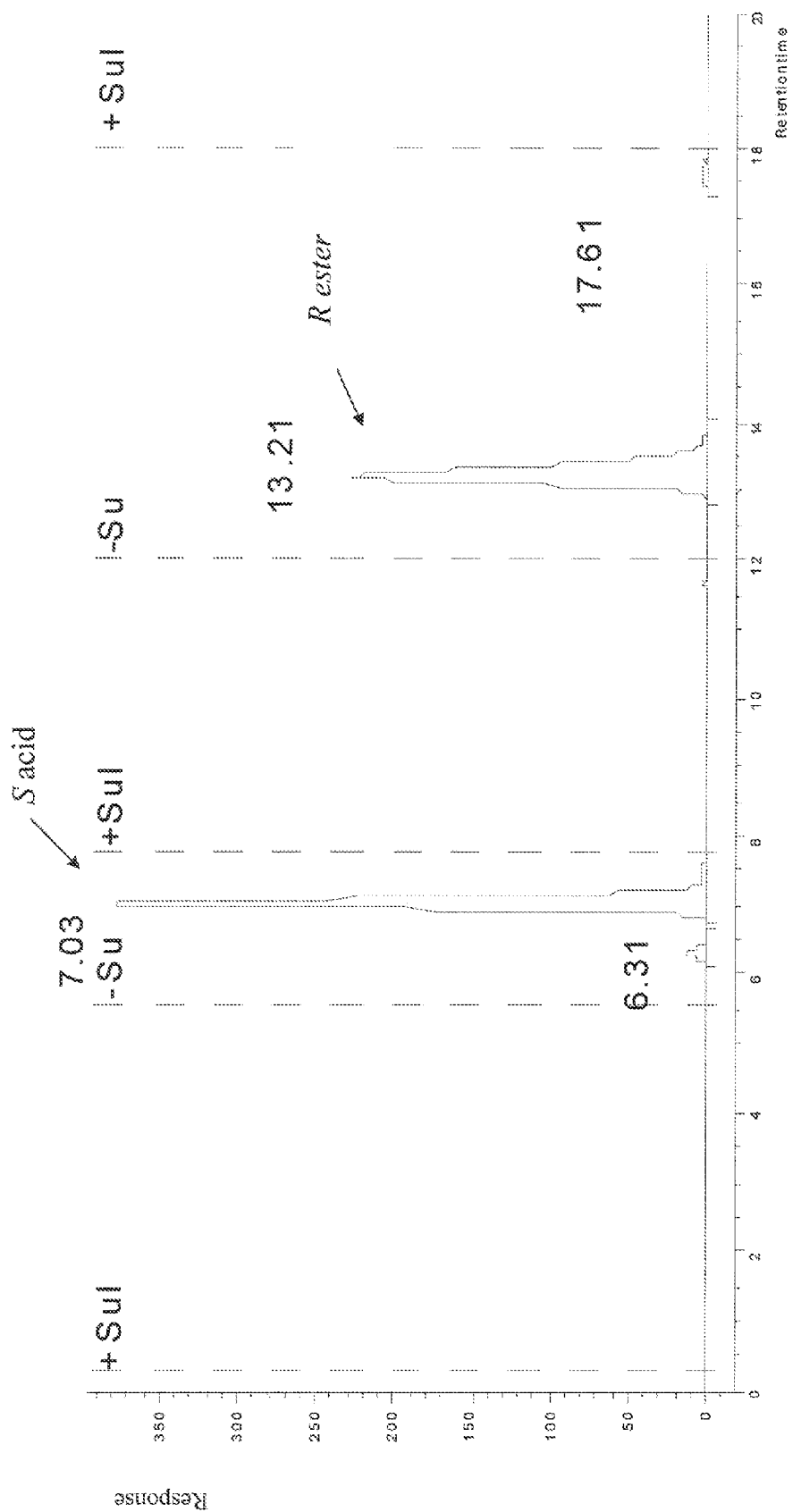
Figure 2 – Enzymatic esterification after 48 hrs.

PROCESS FOR THE ENZYMATIC SYNTHESIS OF (7S)-3,4-DIMETHOXYBICYCLO[4.2.0]OCTA-1,3,5-TRIENE-7-CARBOXYLIC ACID OR ESTERS THEREOF, AND APPLICATION IN THE SYNTHESIS OF IVABRADINE AND SALTS THEREOF

The present invention relates to a process for the enzymatic synthesis of the compound of formula (I):

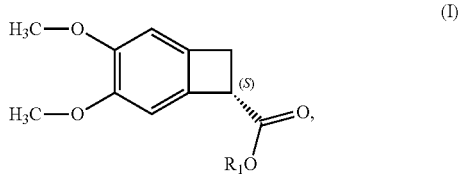

wherein $R_1$ represents a hydrogen atom or a $C_1$-$C_6$alkyl group, preferably methyl, and also to its application in the synthesis of ivabradine of formula (II):

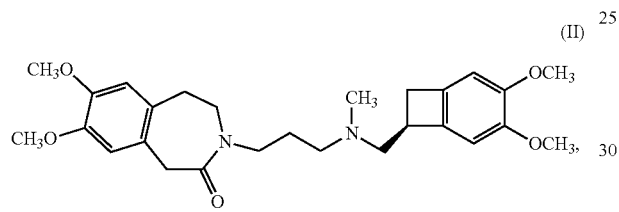

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one,
its addition salts with a pharmaceutically acceptable acid and their hydrates.

Ivabradine, and addition salts thereof with a pharmaceutically acceptable acid, and more especially the hydrochloride thereof, have very valuable pharmacological and therapeutic properties, especially bradycardic properties, which render those compounds useful in the treatment or prevention of various clinical conditions of myocardial ischaemia, such as angina pectoris, myocardial infarction and associated rhythm disorders, as well as in various pathologies involving rhythm disorders, especially supraventricular rhythm disorders, and in heart failure.

The preparation and therapeutic use of ivabradine and addition salts thereof with a pharmaceutically acceptable acid, and more especially the hydrochloride thereof, have been described in European patent specification EP 0 534 859.

That patent specification describes the synthesis of ivabradine hydrochloride starting from the compound of formula (III), (7S)-1-(3,4-dimethoxybicyclo[4.2.0]octa-1,3,5-trien-7-yl) N-methyl methanamine:

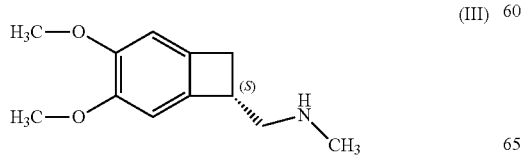

The compound of formula (III) is a key intermediate in the synthesis of ivabradine and its pharmaceutically acceptable salts.

The prior art discloses several methods for obtaining the compound of formula (III).

Patent specification EP 0 534 859 describes the synthesis of the compound of formula (III) by reduction of the racemic nitrile of formula (IV):

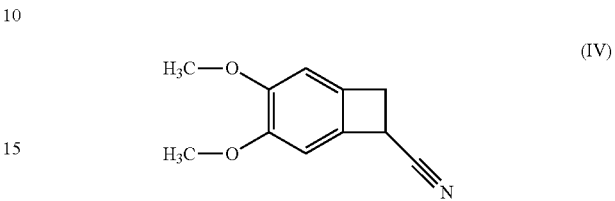

by $BH_3$ in tetrahydrofuran, followed by addition of hydrochloric acid, to yield the hydrochloride of the racemic amine of formula (V):

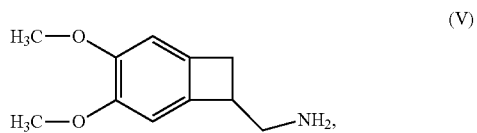

which is reacted with ethyl chloroformate to yield the carbamate of formula (VI):

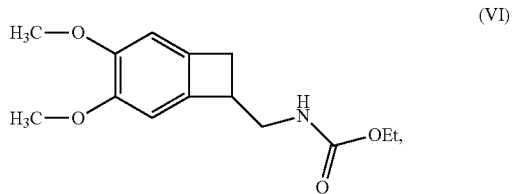 [SMILES: CCOC(=O)NCC1Cc2cc(OC)c(OC)cc21]

the reduction of which, by $LiAlH_4$, yields the racemic methylated amine of formula (VII):

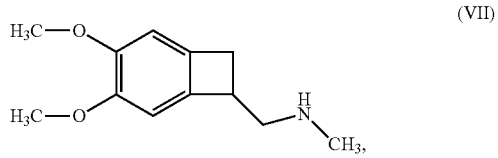

the resolution of which, using camphorsulphonic acid, yields the compound of formula (III). That method has the disadvantage of yielding the compound of formula (III) in only a very low yield of 2 to 3% starting from the racemic nitrile of formula (IV).

That very low yield is due to the low yield (4 to 5%) of the step of resolution of the secondary amine of formula (VII).

Patent specification EP 1 598 333 describes obtaining the compound of formula (III) by resolution of the racemic primary amine of formula (V) into the optically active amine of formula (VIII):

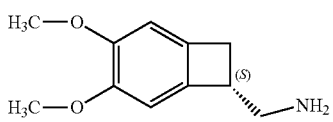

(VIII)

using N-acetyl-L-glutamic acid, followed by methylation using the same reaction sequence as above (conversion into the carbamate, followed by reduction).

The yield of the resolution step is 39%.

Patent specification EP 2 166 004 describes obtaining the compound of formula (III) by optical resolution of the racemic nitrile of formula (IV) by chiral chromatography to yield the optically pure nitrile of formula (IX):

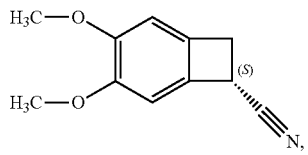

(IX)

which is reduced by NaBH$_4$ to yield the primary amine of formula (VIII), which is then methylated using the same reaction sequence as above (conversion into the carbamate, followed by reduction).

The yield of the resolution step is 45%.

The problem of the present invention was to obtain the compound of formula (III) using an effective process, especially having a good yield, more especially for the resolution step.

The use of biocatalysis for enabling chiral molecules to be obtained appears to be increasingly valuable as an alternative to traditional organic synthesis. Indeed, the use of enzymes which have intrinsic natural properties such as chemo-, regio- and stereo-selectivity makes it possible for enzymes to be used as reagents in green chemistry that has respect for the environment.

In the case described herein, the use of hydrolytic enzymes (hydrolases), which function without cofactors, such as lipases (EC 3.1.1.3 in the international classification of enzymes) or esterases (EC 3.1.1.1) makes it possible to obtain chiral compounds—key intermediates in the synthesis of pharmaceutical active ingredients—in high enantiomeric excesses and good yields.

More specifically, the present invention relates to a process for the synthesis of the optically pure compound of formula (Ia):

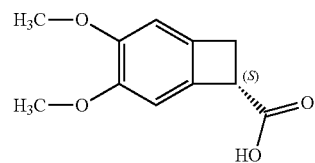

(Ia)

by enantioselective enzymatic esterification of the racemic, or other not optically pure, acid of formula (X):

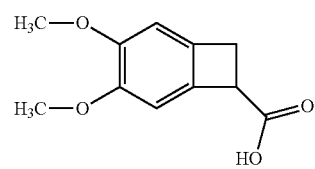

(X)

using a lipase or esterase,
in a mixture of alcohol ROH wherein R represents a linear or branched $C_1$-$C_6$alkyl group, and an organic co-solvent,
at a concentration from 5 to 500 g/L, preferably from 100 g to 200 g of compound of formula (X) per liter of solvent mixture,
at an E/S ratio of from 10/1 to 1/100, preferably from 1/5 to 1/10,
at a temperature from 25° C. to 40° C.

Among the lipases and esterases which may be used in the enzymatic esterification process according to the present invention there may mentioned, without implying any limitation, the lipases of *Candida antarctica*, of *Pseudomonas fluorescens*, of *Pseudomonas cepacia*, of *Rhizopus oryzae*, of *Aspergillus niger*, of *Mucor javanicus*, of *Aspergillus oryzae* and of *Penicillium camemberti*, and the esterases of *Rhizopus oryzae*, of *Mucor miehei* and of *Rhizopus niveus*.

Lipases that are preferred according to the invention are the lipases of *Candida antarctica* and of *Pseudomonas fluorescens*.

Among the lipases of *Candida antarctica* there may be mentioned, by way of example, the lipases immobilised on a polymeric matrix, especially on an acrylic resin, such as Novozym® 435 from the company Novozymes or SPRIN adsorbed CALB® from the company Sprin Technologies, or on a polystyrene resin, such as SPRIN actiplus CALB®, SPRIN acti CALB® or SPRIN lipo CALB® from the company Sprin Technologies, or on an acrylic epoxy resin, such as SPRIN epobond CALB® from the company Sprin Technologies.

The alcohol ROH is preferably methanol or ethanol. The co-solvents are preferably acetonitrile, toluene, MTBE or n-heptane. The preferred cosolvent/alcohol ratio is from 8/2 to 9/1.

The enzymatic esterification scheme according to the invention is as follows:

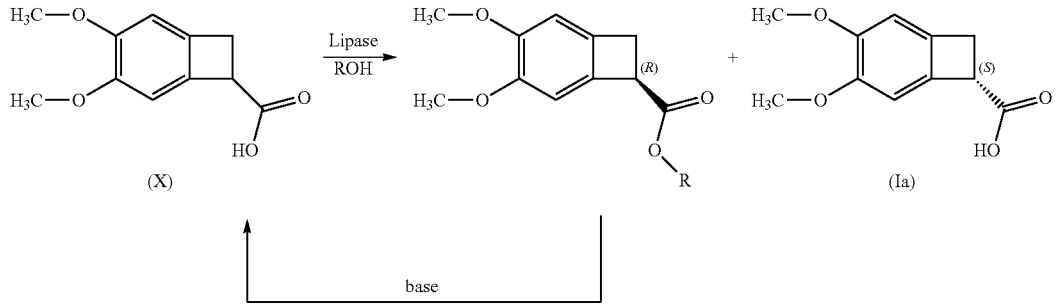

Advantageously, the ester of configuration (R), the secondary product of the reaction, can be hydrolysed by the action of a base, preferably KOH, DBU, triethylamine, DABCO, TBD, sodium ethoxide, sodium methoxide or $K_2CO_3$, to form the racemic acid of formula (X) in order to be recycled into the enzymatic esterification process.

When the hydrolysis/racemisation step is carried out in situ, the process according to the invention is a dynamic kinetic resolution (DKR) process which makes it possible to obtain the S acid of formula (Ia) in an ee≥98% and a yield≥65%.

The acid of formula (Ia) is preferably isolated from the reaction mixture after one or more enzymatic esterification cycles.

Another aspect of the invention relates to a process for the synthesis of the optically pure compound of formula (Ib):

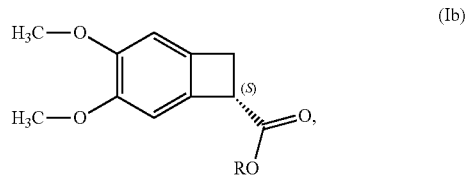
(Ib)

wherein R represents a linear or branched $C_1$-$C_6$alkyl group, preferably methyl or ethyl, by enantioselective enzymatic hydrolysis of the racemic, or other not optically pure, ester of formula (XI):

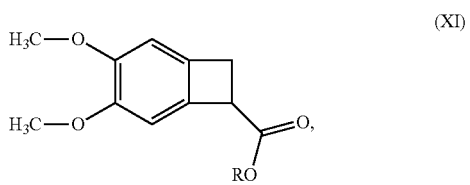
(XI)

wherein R represents a linear or branched $C_1$-$C_6$alkyl group, using a lipase or esterase, in water, in a buffer solution of pH=5 to 8 or in a mixture of organic solvent and water or buffer of pH=5 to 8, at a concentration of from 1 to 200 g/L, preferably about 100 g of compound of formula (XI) per liter of solvent or solvent mixture,
at an E/S ratio of from 10/1 to 1/100, preferably from 1/5 to 1/10,
at a temperature from 25° C. to 40° C.,
followed by isolation of the ester of formula (Ib).

Among the lipases and esterases which may be used in the enzymatic hydrolysis process according to the present invention there may mentioned, without implying any limitation, the lipases of *Candida antarctica*, of *Pseudomonas fluorescens*, of *Pseudomonas cepacia*, of *Rhizopus oryzae*, of *Aspergillus niger*, of *Mucor javanicus*, of *Aspergillus oryzae* and of *Penicillium camemberti*, and the esterases of *Rhizopus oryzae*, of *Mucor miehei* and of *Rhizopus niveus*.

Lipases that are preferred according to this aspect of the invention are the lipases of *Candida antarctica* and of *Pseudomonas fluorescens*.

Among the lipases of *Candida antarctica* there may be mentioned, by way of example, the lipases immobilised on a polymeric matrix, especially on an acrylic resin, such as Novozym® 435 from the company Novozymes or SPRIN adsorbed CALB® from the company Sprin Technologies, or on a polystyrene resin, such as SPRIN actiplus CALB®, SPRIN acti CALB® or SPRIN lipo CALB® from the company Sprin Technologies, or on an acrylic epoxy resin, such as SPRIN epobond CALB® from the company Sprin Technologies.

When the reaction is carried out in the presence of an organic solvent, the latter is preferably acetonitrile, toluene, MTBE or n-heptane.

The preferred organic solvent/water or buffer ratio ranges from 8/2 to 9/1.

The enzymatic hydrolysis scheme according to the invention is as follows:

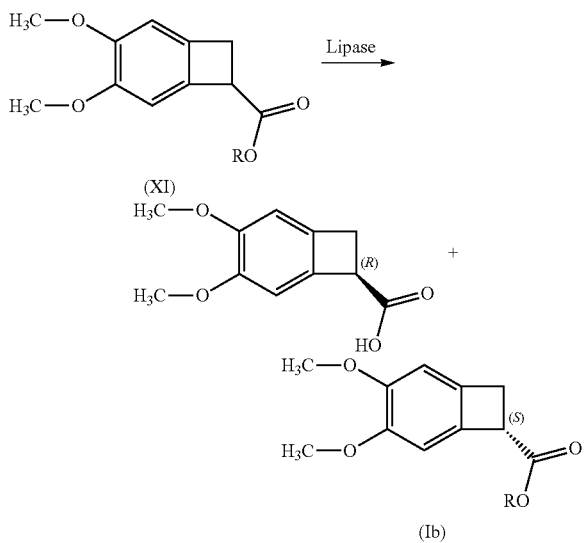

Advantageously, the acid of configuration (R), the secondary product of the reaction, can be racemised by the action of a base, preferably by the action of KOH in the hot state, and then the racemic acid thereby obtained can be alkylated to form the racemic ester of formula (XI) in order to be recycled into the enzymatic hydrolysis process.

Alternatively, the acid of configuration (R), the secondary product of the reaction, can first be alkylated and then the ester of configuration (R) thereby obtained can be racemised by the action of a base, preferably by the action of DBU, KOH, triethylamine, DABCO, TBD, sodium ethoxide, sodium methoxide or $K_2CO_3$, in order to be recycled into the enzymatic hydrolysis process.

When the racemisation is carried out in the hot state, the temperature is preferably from 50 to 80° C.

DEFINITIONS

An optically pure compound is understood to be a compound having an enantiomeric excess greater than or equal to 90%.

An acid or ester which is not optically pure is understood to be an acid or ester having an enantiomeric excess less than 90%.

A racemic acid or ester is understood to be the acid or ester in the form of a mixture of two enantiomers in a ratio of from 55:45 to 45:55.

Enantioselective esterification of a racemic, or other not optically pure, acid is understood to be preferential esterification of one of the enantiomers of the mixture.

Enantioselective hydrolysis of a racemic, or other not optically pure, ester is understood to be preferential hydrolysis of one of the enantiomers of the mixture.

Another aspect of the invention relates to a process for the synthesis of the compound of formula (III) starting from the nitrile of formula (IV), which is hydrolysed to form the racemic acid of formula (X), the enzymatic esterification of which according to the invention yields the optically pure acid of formula (Ia), which is then converted into the optically pure amide of formula (XII):

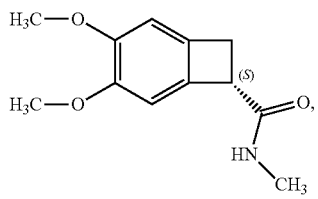
(XII)

the reduction of which, preferably by BH$_3$, NaBH$_4$ or LiAlH$_4$, yields the compound of formula (III).

Another aspect of the invention relates to a process for the synthesis of the compound of formula (III) starting from the nitrile of formula (IV), which is hydrolysed to form the racemic acid of formula (X), and then alkylated to form the racemic ester of formula (XI), the enzymatic hydrolysis of which according to the invention yields the optically pure ester of formula (Ib), which is converted into the optically pure amide of formula (XII):

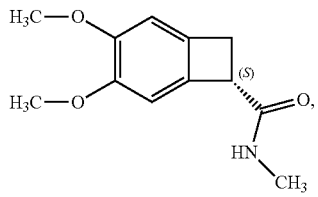
(XII)

the reduction of which, preferably by BH$_3$, NaBH$_4$ or LiAlH$_4$, yields the compound of formula (III).

The compound of formula (III) is subsequently either coupled with a compound of formula (XIII):

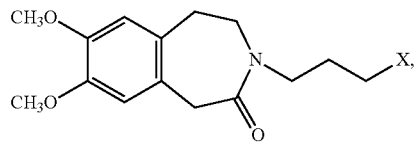
(XIII)

wherein X represents a halogen atom, preferably an iodine atom, or subjected to a reductive amination reaction with a compound of formula (XIV) in the presence of a reducing agent:

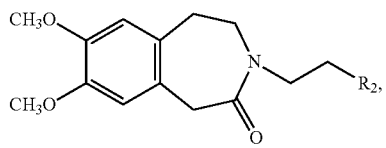
(XIV)

wherein R$_2$ represents a group selected from CHO and CHR$_3$R$_4$, wherein R$_3$ and R$_4$ each represent a linear or branched (C$_1$-C$_6$)alkoxy group or form, together with the carbon atom carrying them, a 1,3-dioxane, 1,3-dioxolane or 1,3-dioxepane ring, to yield ivabradine, which is then converted into an addition salt with a pharmaceutically acceptable acid, said salt being in anhydrous or hydrate form.

The compound of formula (III) may also be used in the reductive amination reaction in the form of its addition salt with a pharmaceutically acceptable acid, preferably its hydrochloride. In that case, ivabradine is obtained directly in the form of the hydrochloride.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

Among the reducing agents that may be used for the reductive amination reaction between the compound of formula (III) and the compound of formula (XIV) there may be mentioned, without implying any limitation, hydride donor compounds such as sodium triacetoxyborohydride or sodium cyanoborohydride, and dihydrogen in the presence of a catalyst such as palladium, platinum, nickel, ruthenium, rhodium or a compound thereof, especially on a support or in the form of oxides.

The preferred reducing agent for the reductive amination reaction between the compound of formula (III) and the compound of formula (XIV) is dihydrogen catalysed by palladium-on-carbon.

BRIEF DESCRIPTION OF THE DRAWINGS

FIG. 1 shows the chiral-phase HPLC chromatogram of the racemic compounds described in Example 2.

FIG. 2 shows the chiral-phase HPLC chromatogram of the product obtained in Example 2.

The Examples hereinbelow illustrate the invention.

ABBREVIATIONS

TFA TriFluoroAcetic acid
TLC Thin-Layer Chromatography
DABCO 1,4-DiAzaBiCyclo[2.2.2]Octane
DBU DiazaBicycloUndecene
DKR Dynamic Kinetic Resolution
E Enantioselectivity coefficient
ee enantiomeric excess
eq molar equivalent
HPLC High Performance Liquid Chromatography
MeOH Methanol
MTBE Methyl Tert-Butyl Ether
op optical or enantiomeric purity
E/S ratio Enzyme/Substrate ratio (g/g)
NMR Nuclear Magnetic Resonance (spectroscopy)
MS Mass Spectrometry
TBD 1,5,7-TriazaBicyclo-[4.4.0]Dec-5-ene
THF TetraHydroFuran
TMS TetraMethylSilane

Example 1

3,4-Dimethoxybicyclo[4.2.0]octa-1,3,5-triene-7-carboxylic acid

Suspend 3,4-dimethoxybicyclo[4.2.0]octa-1,3,5-triene-7-carbonitrile (11 g, 58.1 mmol) in 1N sodium hydroxide solution (70 mL) and reflux (110° C.) the reaction mixture for 2 hours. Allow to return to ambient temperature and then acidify the mixture using concentrated hydrochloric acid. Precipitation is observed.

Dissolve the product in 200 mL of dichloromethane and then extract the aqueous phase. Dry over MgSO₄ and evaporate to yield the title product (11.6 g) in a yield of 95.9%.

Example 2

(7S)-3,4-Dimethoxybicyclo[4.2.0]octa-1,3,5-triene-7-carboxylic acid 0.5 g (c=200 g/L) of racemic acid obtained in Example 1 is dissolved in 2.5 mL of an 8/2 mixture of acetonitrile/methanol.

0.1 g (c=40 g/L) of lipase of *Candida antarctica* NOVOZYM 435® (Novozymes Denmark) is then added to the mixture (E/S ratio 1/5). The reaction mixture is maintained at 30° C., with rotary stirring at 220 rpm, for 48 hours.

The reaction is monitored by chiral-phase HPLC under conditions allowing the enantiomeric excesses of both the ester and the acid to be determined:
Chiralpak® IC 250*4.6 column
30% absolute ethanol+0.1% TFA+70% heptane+0.1% TFA
1 ml/min, 25° C., 288 nm

|         | % acid | % ester | Ee. (%) Acid (S) | Ee (%) Ester (R) | E   |
|---------|--------|---------|------------------|------------------|-----|
| 18 hrs. | 59     | 41      | 66               | >99              | 77  |
| 24 hrs. | 55     | 45      | 78               | >99              | 100 |
| 48 hrs. | 51     | 49      | 97               | >98              | 890 |

The chiral-phase HPLC chromatograms of the racemic compounds, and of the product after 48 hours, are shown in FIGS. 1 and 2.

After 48 hours there is seen the presence of optically pure ester and acid in an optimum acid/ester ratio of close to 50/50. The reaction mixture is filtered, the enzyme is washed with 5 mL of methanol and then the filtrate is evaporated in vacuo. The optically pure S acid and R ester are separated by chromatography on a silica column (eluant: dichloromethane/methanol 98/1).

(S) acid: 0.22 g (44%); optical purity>96%; $[\alpha]^{20}_D$ at 589 nm: +57.1° (5 mg/ml in MeOH) (R) ester: 0.24 g; optical purity>96%; $[\alpha]^{20}_D$ at 589 nm: −62.7° (5 mg/ml in MeOH) Overall yield (S+R): 92%.

Example 3

Methyl 3,4-dimethoxybicyclo[4.2.0]octa-1,3,5-triene-7-carboxylate

Suspend methyl (7R)-3,4-dimethoxybicyclo[4.2.0]octa-1,3,5-triene-7-carboxylate (445 mg) (ee≥96%) in isopropanol (2.5 mL) and add diazabicycloundecene (58 μl-1.5 eq). Heat the reaction mixture at 65° C. for 2 hours. Complete racemisation is observed at the end of 2 hours of reaction of the ester.
Analysis Conditions:
Chiralpak® IC 250*4.6 column
30% absolute ethanol+0.1% TFA+70% heptane+0.1% TFA
1 ml/min, 25° C., 288 nm

Example 4

3,4-Dimethoxybicyclo[4.2.0]octa-1,3,5-triene-7-carboxylic acid

Suspend methyl (7R)-3,4-dimethoxybicyclo[4.2.0]octa-1,3,5-triene-7-carboxylate (50 mg) (ee>96%) in methanol (1 mL) and add potassium hydroxide (56.1) (25 mg-2 eq). Heat the reaction mixture at 65° C. for 6 hours. Hyrdolysis of the ester to the racemic acid is observed.
Analysis Conditions:
Chiralpak® IC 250*4.6 column
30% absolute ethanol+0.1% TFA+70% heptane+0.1% TFA
1 ml/min, 25° C., 288 nm

Example 5

(7S)-3,4-Dimethoxybicyclo[4.2.0]octa-1,3,5-triene-7-carboxylic acid 2 g (c=200 g/L) of racemic 3,4-dimethoxybicyclo[4.2.0]octa-1,3,5-triene-7-carboxylic acid are dissolved in 20 ml of an acetonitrile/methanol mixture (9/1).

0.4 g (c=20 g/L) of lipase of *Candida antarctica* SPRIN actiplus CALB® (Sprin Technologies) is then added to the mixture. The reaction mixture is maintained at 30° C., with rotary stirring at 220 rpm for 24 hours. The enzyme is filtered off and then washed with methanol. 0.5 g of KOH (2 eq) is then added to the mixture (filtrate) and stirring is maintained for 6 hours at 30° C. The mixture is then evaporated in vacuo. This allows complete racemisation and hydrolysis of the R ester without racemising the S acid. The residue is taken up in ethyl acetate and then washed with 10% citric acid solution. Extraction with ethyl acetate not being sufficient, the water-soluble acid is re-extracted with butan-1-ol solution. The extracts are dried over MgSO₄ to yield, after evaporation, 1.9 g of acid having a ratio of 75:25 (S:R). This enantiomerically enriched acid is used in a second enzymatic reaction in the presence of 0.2 g of lipase. After 24 hours at 30° C., the enzyme is filtered off and then washed with methanol.

After evaporation, the residue is chromatographed on a silica column (eluant CH₂Cl₂/MeOH from 99/1 to 99/2) to yield the following products:
(S) acid: 1.33 g; op>96%; yield of acid (theoretically 75%): 67%
(R) ester: 0.42 g; op>96%; yield of ester (theoretically 25%): 21%
The overall yield of the reaction is ∼88%.
NMR and MS Characterisation of the Acid
¹H NMR (DMSO-d6, ppm/TMS): 3.17 (dd; 1H, 13.6 Hz; 2.4 Hz); 3.27 (dd; 1H, 13.6 Hz; 5.3 Hz); 4.13 (dd; 1H); 3.71 (s; 3H); 6.78 (s; 1H); 6.80 (s; 1H); 12.40 (s; 1H).
MS (EI+) Molecular ion M+ at m/z 208.

NMR and MS Characterisation of the Ester $^1$H NMR (DMSO-d6, ppm/TMS)=3.19 (dd; 1H, 13.6 Hz; 2.4 Hz); 3.33 (dd; 1H, 13.6 Hz; 5.5 Hz); 3.65 (s; 3H); 3.71 (s; 6H); 4.23 (dd; 1H); 6.79 (s; 1H); 6.82 (s; 1H).

MS (EI+) Molecular ion M+ at m/z 222.

The sequence of reactions is monitored by chiral-phase HPLC under conditions allowing the enantiomeric excesses of both the ester and the acid to be determined:

Chiralpak® IC 250*4.6 column
30% absolute ethanol+0.1% TFA+70% heptane+0.1% TFA
1 ml/min, 25° C., 288 nm Example 6

Methyl 3,4-dimethoxybicyclo[4.2.0]octa-1,3,5-triene-7-carboxylate

Dissolve 3,4-dimethoxybicyclo[4.2.0]octa-1,3,5-triene-7-carboxylic acid (3 g-14.4 mmol) in methanol and add acetyl chloride (1.65 g-21.1 mmol).

Reflux the reaction mixture for 2 hours. Analysis by TLC (eluant: dichloromethane) shows the absence of the racemic acid starting material.

Evaporate the reaction mixture, take up the residue in ethyl acetate and wash the organic phase with NaHCO$_3$. Evaporate to dryness, and dry to yield the title product in a yield of 97%.

Example 7

Methyl (7S)-3,4-dimethoxybicyclo[4.2.0]octa-1,3,5-triene-7-carboxylate 2 g (c=100 g/L) of racemic methyl 3,4-dimethoxybicyclo[4.2.0]octa-1,3,5-triene-7-carboxylate are dissolved in 20 mL of an 80/20 mixture of acetonitrile/buffer pH=7.

0.4 g (c=20 g/L) of lipase of *Candida antarctica* NOVOZYM 435® (Novozymes Denmark) is then added to the mixture (E/S ratio 1/5). The reaction mixture is maintained at 30° C., with rotary stirring at 230 rpm.

After reacting for 4 hours (pH=5.8), the pH is adjusted to 7.2. After 24 hours, the enzyme is filtered off and washed by stirring in methanol. All the filtrates are collected, evaporated and lyophilised.

The lyophilisate is taken up in ethyl acetate, stirring is maintained overnight and then the reaction mixture is filtered and the filtrate is evaporated.

The residue is purified on a silica column (eluant dichloromethane/methanol) to obtain 0.81 g of the ester of the title (7S), that is to say in a yield of 41%.

$[\alpha]^{20}_D$ at 589 nm: +64.7° (5 mg/ml in MeOH)

The fraction containing the acid is taken up in ethyl acetate to yield 0.72 g of (7R) acid, that is to say in a yield of 36%.

$[\alpha]^{20}_D$ at 589 nm: −58.8° (5 mg/ml in MeOH)

Example 8

Methyl (7S)-3,4-dimethoxybicyclo[4.2.0]octa-1,3,5-triene-7-carboxylate

Racemic methyl 3,4-dimethoxybicyclo[4.2.0]octa-1,3,5-triene-7-carboxylate (1 mg; c=1 g/L) is dissolved in 1 mL of a 90/10 mixture of phosphate buffer pH=7/toluene.

5 mg (c=5 g/L) of lipase of *Pseudomonas fluorescens* are then added to the mixture (E/S ratio 5/1). The reaction mixture is maintained at 28° C., with rotary stirring at 220 rpm, for 48 hours.

The reaction mixture is analysed by reverse-phase HPLC and the enantioselectivity (ee) of the residual ester is monitored by chiral-phase HPLC, in accordance with the methods described below:

Conditions for Analysis of the Reaction Mixture by Reverse-Phase HPLC:

Kinetex® 2.6 µm C18 50*2.1, 40° C., 0.6 ml/min 100% A to 100% B over 5 mins.
A (1000 water+25 ACN+1 TFA)
B (1000 ACN+25 water+1 TFA)

Conditions for Analysis of the Enantioselectivity by Chiral-Phase HPLC:

Chiralpak® IC 250*4.6 column, 100% absolute ethanol, 1 ml/min, 25° C., 288 nm

| Enantiomer | Retention time (min) |
|---|---|
| (7R) | 7.19 |
| (7S) | 9.03 |

Analysis of the reaction mixture shows good hydrolytic activity (percentage of residual ester: 25%).

Analysis of the enantioselectivity shows an ee of 90% for the ester (7S).

Example 9

3,4-Dimethoxybicyclo[4.2.0]octa-1,3,5-triene-7-carboxylic acid

Suspend (7R)-3,4-dimethoxybicyclo[4.2.0]octa-1,3,5-triene-7-carboxylic acid (50 mg-ee>95%) in methanol (1 mL) and add potassium hydroxide (20 mg).

Heat the reaction mixture at 65° C. for 24 hours. Complete racemisation of the acid is observed.

Analysis Conditions:

Chiralpak® IC 250*4.6 column
30% absolute ethanol+0.1% TFA+70% heptane+0.1% TFA
1 ml/min, 25° C., 288 nm Example 10

(7S)-3,4-Dimethoxy-N-methylbicyclo[4.2.0]octa-1,3,5-triene-7-carboxamide

Suspend the (7S)-3,4-dimethoxybicyclo[4.2.0]octa-1,3,5-triene-7-carboxylic acid obtained in Example 5 (300 mg) in THF (3 ml) at ambient temperature and then add triethylamine (200 µl). Ethyl chloroformate (150 µl) is added slowly to the mixture. The reaction mixture precipitates (mixture I).

In another flask, methylamine, as a 2M solution in THF (2.25 ml), is stirred with water (1 ml) and triethylamine (300 µl). Stirring is maintained for 20 minutes and then the resulting mixture is added to mixture I and stirred at ambient temperature overnight.

The reaction mixture is then evaporated and purified by preparative HPLC.

(7S)-3,4-Dimethoxy-N-methylbicyclo[4.2.0]octa-1,3,5-triene-7-carboxamide is obtained in a yield of 60%.

¹H NMR (DMSO-d6, ppm/TMS)=2.61 (m; 3H); 3.16 (m; 2H); 3.71 (s; 6H); 4.05 (m; 1H); 6.78 (s; 1H); 6.81 (s; 1H); 7.78 (s; 1H).

Example 11

(7S)-3,4-Dimethoxy-N-methylbicyclo[4.2.0]octa-1,3,5-triene-7-carboxamide

Suspend methyl (7S)-3,4-dimethoxybicyclo[4.2.0]octa-1,3,5-triene-7-carboxylate (500 mg) in water and then slowly add, at ambient temperature, 20 mL of 33% methylamine solution in absolute ethanol.

After stirring for 3 hours, the reaction mixture is evaporated. The residue obtained is purified by preparative HPLC (eluant: water/acetonitrile/trifluoroacetic acid from 98/2/0.2 to 20/80/0.2) over 30 minutes to yield the title product in a yield of 70%.

Example 12

(7S)-3,4-Dimethoxybicyclo[4.2.0]octa-1,3,5-trien-7-yl]-N-methyl-methanamine

Suspend (7S)-3,4-dimethoxy-N-methylbicyclo[4.2.0]octa-1,3,5-triene-7-carboxamide (450 mg) in tetrahydrofuran (20 mL) and then slowly add 1.6 mL of 2M LiAlH$_4$ solution in tetrahydrofuran to the reaction mixture at ambient temperature. Marked evolution of gas is observed and the reaction mixture becomes clear. Heat the reaction mixture at reflux for 30 minutes.

After returning to ambient temperature, hydrolyse and then extract with ethyl acetate. Dry over MgSO$_4$ and then evaporate. The residue obtained is purified by preparative HPLC (eluant: water/acetonitrile/trifluoroacetic acid from 98/2/0.2 to 20/80/0.2) over 30 minutes to yield the title product in a yield of 46%.

¹H NMR (DMSO-d6, ppm/TMS)=2.60 (m; 3H); 2.85 (m; 1H); 3.15 (m; 1H); 3.25 (dd; 1H); 3.30 (m; 1H); 3.62 (m; 1H); 3.70 (s; 6H); 6.82 (s; 1H); 6.89 (s; 1H); 8.48 (s; 1H).

Example 13

(7S)-3,4-Dimethoxybicyclo[4.2.0]octa-1,3,5-trien-7-yl]-N-methyl-methanamine hydrochloride 20 mL of a molar solution of BH$_3$ in tetrahydrofuran are added, at ambient temperature, to a mixture of 2.2 g (10 mmol) of (7S)-3,4-dimethoxy-N-methylbicyclo[4.2.0]octa-1,3,5-triene-7-carboxamide in 45 mL of tetrahydrofuran. After stirring for 1 hour, 10 mL of the solution of BH$_3$ in tetrahydrofuran are added. After stirring overnight at ambient temperature, 20 mL of ethanol are added dropwise and the mixture is stirred until no more gas is evolved (about 1 hour). 20 mL of hydrochloric acid solution in ethanol are then added dropwise. After stirring for 4 hours, the precipitate obtained (1.2 g of the title product) is filtered off. The filtrate is concentrated and an additional 0.65 g of the title product is obtained by rendering it solid in an 80/20 mixture of ethyl acetate/ethanol.

The two precipitates are combined to yield 1.85 g of the title product (yield: 77%).

Example 14

Ivabradine Hydrochloride

Load 5.5 kg of 3-[2-(1,3-dioxolan-2-yl)ethyl]-7,8-dimethoxy-1,3-dihydro-2H-3-benz azepin-2-one, 27.5 liters of ethanol and 550 g of palladium-on-carbon into an autoclave. Purge with nitrogen and then with hydrogen, heat to 55° C., and then hydrogenate at that temperature under a pressure of 5 bars until the theoretical amount of hydrogen has been absorbed.

Then return to ambient temperature and depressurise the autoclave.

Then add 4 kg of (7S)-3,4-dimethoxybicyclo[4.2.0]octa-1,3,5-trien-7-yl]-N-methyl-methanamine hydrochloride, 11 liters of ethanol, 5.5 liters of water and 1 kg of palladium-on-carbon.

Purge with nitrogen and then with hydrogen, heat to 85° C., and then hydrogenate at that temperature under a pressure of 30 bars until the theoretical amount of hydrogen has been absorbed.

Then bring back to ambient temperature, purge the autoclave and then filter the reaction mixture; distil off the solvents and then isolate the ivabradine hydrochloride by crystallisation from a toluene/1-methyl-2-pyrrolidinone mixture.

Ivabradine hydrochloride is thereby obtained in a yield of 85% and with a chemical purity greater than 99%.

Comparative Example

Screening of Lipases an Esterases for the Enzymatic Hydrolysis of methyl 3,4-dimethoxybicyclo[4.2.0]octa-1,3,5-triene-7-carboxylate Racemic methyl 3,4-dimethoxybicyclo[4.2.0]octa-1,3,5-triene-7-carboxylate (1 mg; c=1 g/L) is dissolved in 1 mL of a 90/10 mixture of phosphate buffer pH=7/toluene.

5 mg (c=5 g/L) of the lipase or esterase being studied are then added to the medium (E/S ratio 5/1). The reaction mixture is maintained at 28° C., with rotary stirring at 220 rpm for 48 hours.

The reaction mixture is analysed by reverse-phase HPLC and the enantioselectivity (ee) of the residual ester is monitored by chiral-phase HPLC, in accordance with the methods described hereinbelow:

Conditions for Analysis of the Reaction Mixture by Reverse-Phase HPLC:

Kinetex® 2.6 μm C18 50*2.1, 40° C., 0.6 ml/min 100% A to 100% B over 5 minutes

A (1000 water+25 ACN+1 TFA)

B (1000 ACN+25 water+1 TFA)

Conditions for Analysis of the Enantioselectivity by Chiral-Phase HPLC:

Chiralpak® IC 250*4.6 column 100% absolute ethanol, 1 ml/min, 25° C., 288 nm

| Enantiomer | Retention time (min) |
| --- | --- |
| (7R) | 7.19 |
| (7S) | 9.03 |

The results are summarised in the following table:

| Lipase | % ester | % acid | Ee$^a$ (%) ester | E$^b$ |
| --- | --- | --- | --- | --- |
| Porcine Pancreatic Lipase Type II | — | 100 | 0 | — |
| Lipase PS (*Pseudomonas cepacia*) | 55 | 45 | 34 (S enantio) | 3 |
| Lipase AY 30 (*Candida rugosa*) | — | 100 | 0 | — |
| Lipase FAP-15 (*Rhizopus oryzae*) | 45 | 55 | 52 (S enantio) | 4 |
| Lipase A6 (*Aspergillus niger*) | 76 | 24 | 68 (R enantio) | 6 |
| Lipase AH (*Pseudomonas cepacia*) | 90 | 10 | 14 (S enantio) | 8 |

-continued

| Lipase | % ester | % acid | Ee$^a$ (%) ester | E$^b$ |
|---|---|---|---|---|
| Lipase M "Amano"10 (*Mucor javanicus*) | 60 | 40 | 36 (S enantio) | 5 |
| Lipase of *Aspergillus oryzae* | 78 | 22 | 64 (S enantio) | 5 |
| Lipase G "Amano" (*Penicillium camemberti*) | 40 | 60 | 26 (R enantio) | 2 |
| Lipase AYS "Amano" (*Candida rugosa*) | 60 | 40 | 4 (R enantio) | 1 |
| Lipase R "Amano" (*Penicillium roqueforti*) | — | 100 | 0 | |
| Porcine liver esterase | — | 100 | 0 | |
| Esterase of *Rhizopus oryzae* | 40 | 60 | 50 (S enantio) | 3 |
| Esterase of *Mucor miehei* | 79 | 21 | 45 (S enantio) | 6 |
| Horse liver esterase | — | 100 | 0 | |
| Newlase F (*Rhizopus niveus*) | — | 100 | 0 | — |
| Lipase of *Pseudomonas fluorescens* | 25 | 75 | 90 (S enantio) | 6 |
| Lipase B of *Candida antarctica* (Novozym® 435) | 30 | 70 | 94 (S enantio) | 9 |

$^a$Enantiomeric excess ee (en %) = % enantioE2 − % enantioE1/% enantio E2 + % enantio E1 (enantio E2 being the predominant enantiomer)
$^b$Enantioselectivity coefficient E = ln[(1 − c)(1 − ee(S)]/ln[(1 − c)(1 + ee(S)]; c = level of conversion = ee(ester)/ee(ester) + ee(acid)

The invention claimed is:

1. A process for the synthesis of an optically pure compound of formula (Ia):

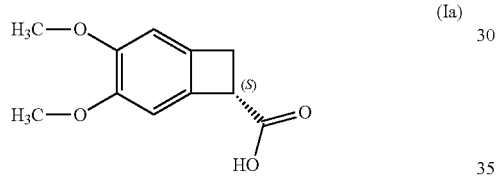

by enantioselective enzymatic esterification of a racemic, or other not optically pure, acid of formula (X):

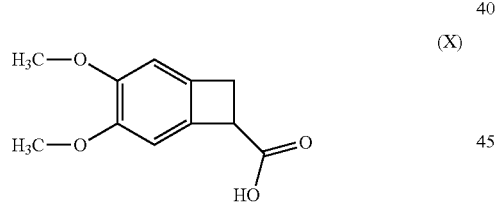

using a lipase of *Candida antarctica*
in a mixture of an alcohol of formula ROH wherein R represents a linear or branched $C_1$-$C_6$ alkyl group, and an organic co-solvent,
at a concentration from 5 to 500 g/L of compound of formula (X) per liter of solvent mixture,
at an Enzyme/Substrate (E/S) ratio of from 10/1 to 1/100,
at a temperature from 25° C. to 40° C.

2. The process according to claim 1, wherein the E/S ratio is from 1/5 to 1/10.

3. The process according to claim 1, wherein the alcohol of formula ROK is methanol and the co-solvent is acetonitrile.

4. The process according to claim 3, wherein the acetonitrile/methanol ratio is from 8/2 to 9/1.

5. The process according to claim 1, wherein a secondary product of the reaction, an ester of configuration (R):

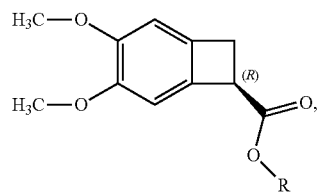

wherein R represents a linear or branched $C_1$-$C_6$ alkyl group,
is obtained, which ester is hydrolysed by the action of a base to form the racemic acid of formula (X) in order to be recycled into the enzymatic esterification process.

6. The process according to claim 5, wherein the base is KOH.

7. The process according to claim 5, wherein the hydrolysis/racemisation step is carried out in situ.

8. The process according to claim 1, wherein the acid of formula (Ia) is isolated after one or more cycles of enzymatic esterification.

9. A process for the synthesis of a compound of formula (III):

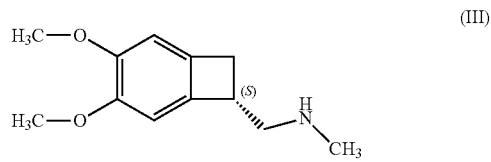

starting from a nitrile of formula (IV):

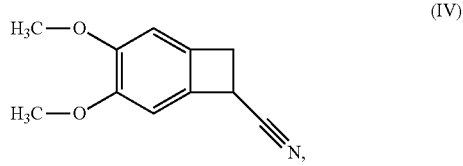

which is hydrolysed to form a racemic acid of formula (X):

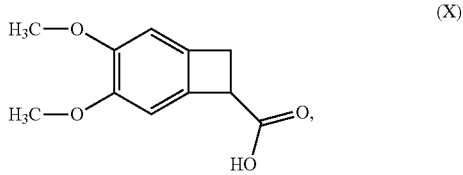

the enzymatic esterification of which in accordance with claim 1 yields an optically pure acid of formula (Ia):

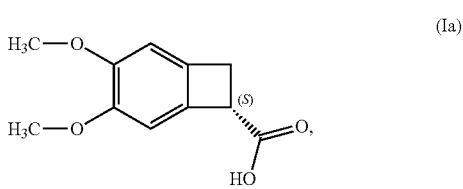

which is then converted into an optically pure amide of formula (XII):

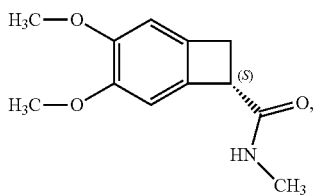

(XII)

the reduction of which yields the compound of formula (III).

10. The process according to claim 9, wherein the reduction of the compound of formula (XII) to form the compound of formula (III) is carried out by BH$_3$, NaBH$_4$ or LiAlH$_4$.

11. The process according to claim 9, wherein the compound of formula (III) is subsequently either coupled with a compound of formula (XIII)

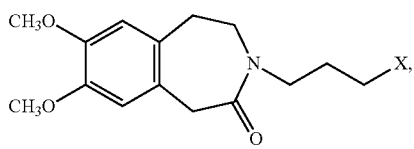

(XIII)

wherein X represents a halogen atom,
or subjected to a reductive amination reaction with a compound of formula (XIV) in the presence of a reducing agent:

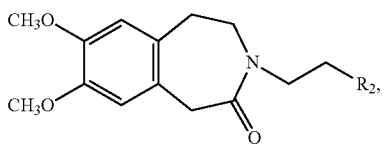

(XIV)

wherein R$_2$ represents a group selected from CHO and CHR$_3$R$_4$,
wherein R$_3$ and R$_4$ each represent a linear or branched (C$_1$-C$_6$)alkoxy group or form, together with the carbon atom carrying them, a 1,3-dioxane, 1,3-dioxolane or 1,3-dioxepane ring,
to yield ivabradine, which is then converted into an addition salt with a pharmaceutically acceptable acid, said salt being in anhydrous or hydrate form.

12. The process according to claim 11, wherein the compound of formula (III) is used in the reductive amination reaction in the form of its hydrochloride to yield ivabradine in the form of the hydrochloride.

13. The process according claim 11, wherein the reductive amination reaction with a compound of formula (XIV) is carried out in the presence of dihydrogen catalysed by palladium-on-carbon.

\* \* \* \* \*

UNITED STATES PATENT AND TRADEMARK OFFICE
CERTIFICATE OF CORRECTION

PATENT NO. : 9,506,095 B2  
APPLICATION NO. : 13/759382  
DATED : November 29, 2016  
INVENTOR(S) : Sandrine Pedragosa-Moreau and François Lefoulon Page 1 of 1

It is certified that error appears in the above-identified patent and that said Letters Patent is hereby corrected as shown below:

On the Title Page

Item (73), Assignee: "LES LABORATORIES SERVIER" should be
--LES LABORATOIRES SERVIER--.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*